(12) United States Patent
Bravo Lamicq et al.

(10) Patent No.: US 12,029,727 B2
(45) Date of Patent: Jul. 9, 2024

(54) COMBINATIONS AND METHODS FOR THE TREATMENT OF NEUROPATHIC PAIN

(71) Applicant: CIDAT, S.A. DE C.V., Mexico City (MX)

(72) Inventors: Elia Cecilia Bravo Lamicq, Mexico City (MX); Juana Edith Zárate Rodríguez, Mexico City (MX)

(73) Assignee: CIDAT, S.A. DE C.V., Mexico City (MX)

( * ) Notice: Subject to any disclaimer, the term of this patent is extended or adjusted under 35 U.S.C. 154(b) by 29 days.

(21) Appl. No.: 16/469,277

(22) PCT Filed: Dec. 14, 2016

(86) PCT No.: PCT/MX2016/000137
§ 371 (c)(1),
(2) Date: Jun. 13, 2019

(87) PCT Pub. No.: WO2018/111060
PCT Pub. Date: Jun. 21, 2018

(65) Prior Publication Data
US 2020/0101043 A1    Apr. 2, 2020

(51) Int. Cl.
*A61K 31/385* (2006.01)
*A61K 9/00* (2006.01)
*A61K 31/197* (2006.01)

(52) U.S. Cl.
CPC .......... *A61K 31/385* (2013.01); *A61K 9/0053* (2013.01); *A61K 31/197* (2013.01)

(58) Field of Classification Search
CPC .. A61K 31/197; A61K 31/385; A61K 9/0053; A61K 2300/00; A61P 25/02
See application file for complete search history.

(56) References Cited

U.S. PATENT DOCUMENTS

2011/0129442 A1    6/2011 Magri et al.
2016/0058752 A1    3/2016 Aung-Din

OTHER PUBLICATIONS

He, Curative effects of alpha-lipoic acid combined with pregabalin on diabetic peripheral neuropathy. Zhougguo Manxingbing Yufang Yu Kongzhi, vol. 21(2), pp. 172-174 (English Abstract) (Year: 2013).*
He, "Therapeutic effectes of alpha-lipoic acid combined with pregabalin on diabetic peripheral neuropathy", Chin J. Prew Contr Chron Dis, vol. 21(2), 172-174 (Year: 2013), English translation.*
Richter et al., Relief of Painful Diabetic Peripheral Neuropathy With Pregabalin: A Randomized, Palcebo-Controlled Trial. The Journal of Pain, vol. 6(4), pp. 253-260 (Year: 2005).*
Patel et al., A study of the use of carbamazepine, pregabalin and alpha lipoic acid in patients of diabetic neuropathy. J. Diabetes & Metabolic Disorders, vol. 13(62), pp. 1-7 (Year: 2014).*
Attal, "Neuropathic Pain: Mechanisms, Therapeutic Approach, and Interpretation of Clinical Trials", Continuum Lifelong Learning Neurology, 2012; vol. 18, No. 1, pp. 161-175.
Baron, "Neuropathic Pain: A Clinical Perspective", Handbook of Experimental Pharmacology 194, 2009; pp. 3-30.
Descalzi et al., "Epigenetic Mechanisms of Chronic Pain", Trends Neuroscience, 2015; vol. 38, No. 4, pp. 237-246.
Dworkin et al., "Pharmacologic Management of Neuropathic Pain: Evidence-Based Recommendations", Pain, 2007; vol. 132, No. 3, pp. 237-251.
Guevara-Lopez et al., "Parametros de practica para, el manejo del dolor neuropatico", Revista de Investigacion Clinica, 2006; vol. 58, No. 2, pp. 126-138, Abstract only.
International Search Report for PCT/MX2016/000137 dated May 5, 2017 (2 pages).
Written Opinion (WO) for PCT/MX2016/000137 dated May 5, 2017 (5 pages).
International Preliminary Report on Patentability (IPRP) for PCT/MX2016/000137 dated Apr. 2, 2019 (13 pages).
Vasudevan et al., "Efficacy and Safety of Methylcobalamin, Alpha Lipoic Acid and Pregabalin Combination Versus Pregabalin Monotherapy in Improving Pain and Nerve Conduciton Velocity in Type 2 Diabetes Associated Impaired Peripheral Neuropathic Condition", Annals of Indian Academy of Neurology (2014).

* cited by examiner

*Primary Examiner* — Barbara P Badio
(74) *Attorney, Agent, or Firm* — Shumaker, Loop & Kendrick, LLP

(57) ABSTRACT

A method of treatment of neuropathic pain by co-administering alpha lipoic acid and pregabalin, and a pharmaceutical composition including a combination of alpha lipoic acid and pregabalin, the pharmaceutical composition being useful for treatment of neuropathic pain.

4 Claims, 4 Drawing Sheets

COMBINATIONS AND METHODS FOR THE TREATMENT OF NEUROPATHIC PAIN

FIELD OF INVENTION

The present invention belongs to the field of medicine, particularly to a therapeutic treatment of neuropathic pain.

BACKGROUND OF THE INVENTION

Neuropathic pain is a chronic pain state which may remain for long time after repairing the damage which caused it. According to the International Association for Pain Study, neuropathic pain may be defined as that pain caused by any injury or dysfunction located in somatic sensory nervous system. Adults with chronic pain in the United States are estimated in about 100 million persons, with an annual cost of 635 billion dollars per year (Descalzi G, Ikegami D, Ushijima T, Nestler E J, Zachariou V, Narita M. Epigenetic mechanisms of chronic pain. Trends Neurosci. 2015; 38(4):237-46). In Mexico, it is estimated that about 2 million persons suffer from neuropathic pain, however, these figures may be underestimated (Guevara-López U, Covarrubias-Gómez A, Garcia-Ramos G, Hernández-Jiménez S. 2006a. Grupo de Consenso para el Manejo del Dolor Neuropático. Parámetros de práctica para el manejo de dolor neuropático. Rev Invest Clin. 58(2):126-38). Neuropathic pain is present in various etiology disorders and is often difficult to treat while life quality of the patients who suffer it is enormously affected. In some patients, a nerve injury spontaneously generates a constant pain sensation which often is described as burning pain; or an intermittent pain perceived as a shot or electric shock. Moreover, the neuropathic pain is characterized by a remarkable reduction in stimulation thresholds required for inducing pain, so that innocuous stimuli such as touch may cause pain (allodynia) and painful stimuli generate an excessive unpleasant response (hyperalgesia).

Current clinical treatment for neuropathic pain includes the use of antidepressants, anticonvulsants and local anesthetics as first line drugs, while opioids are used as second or third line drugs for treatment. However, current therapeutics nowadays results in limited efficacy and is far from being fully safe (Attal N. 2012. Neuropathic pain: mechanisms, therapeutic approach, and interpretation of clinical trials. Continuum (Minneap Minn). 18(1):161-75; Baron R. 2009. Neuropathic pain: a clinical perspective. Handb Exp Pharmacol. 194:3-30; Dworkin R H. 2007. Pharmacologic management of neuropathic pain: evidence-based recommendations. Pain. 132(3):237-51). Therefore there is a need of searching therapeutic alternatives which allow developing more efficient and safe treatments for neuropathic pain.

DETAILED DESCRIPTION OF THE INVENTION

Figure 1:
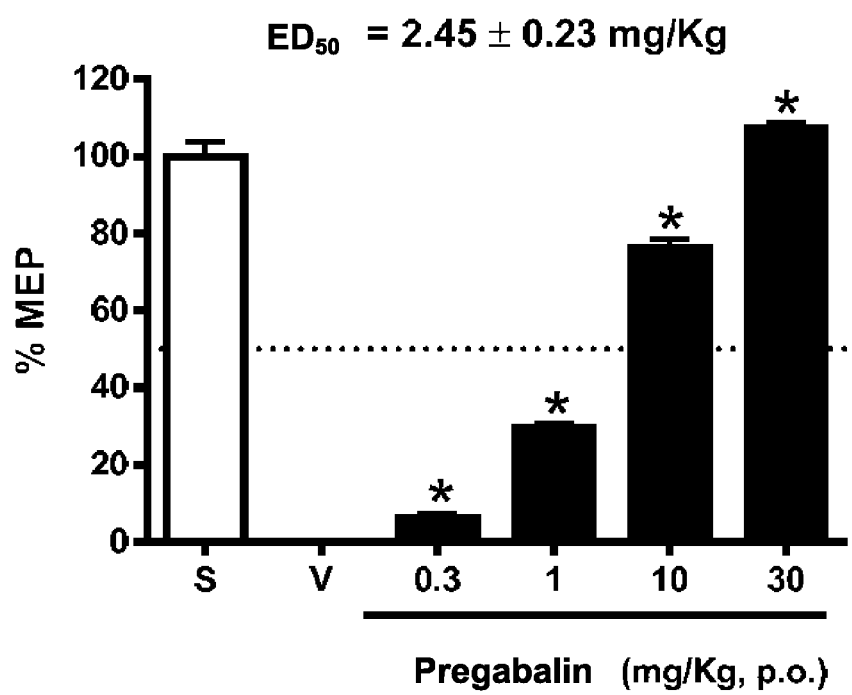
FIG. 1. Dose-response curve showing a percentage of maximum possible anti-neuropathic effect (% MEP) obtained with oral administration of increasing doses of pregabalin in a neuropathic pain model induced by L5/L6 spinal nerve ligation in rats (ED50=2.45±0.23 mg/kg).

In one aspect, the present invention relates to a method of treatment of neuropathic pain, comprising administering alpha lipoic acid and pregabalin.

In another aspect, the present invention provides a pharmaceutical composition comprising a combination of alpha lipoic acid and pregabalin. The pharmaceutical composition of present invention is useful for treatment of neuropathic pain.

Accordingly, in one embodiment the present invention is referred to a method of treatment of neuropathic pain, comprising administering pregabalin and alpha lipoic acid in a synergistically effective amount. A "synergistically effective amount" as used herein, is referred to a pregabalin amount and an alpha lipoic acid amount which therapeutic effect after administered in combination is higher than the sum of therapeutic effects of pregabalin and alpha lipoic acid after administered separately.

In one embodiment, the method of treatment of the invention comprises administering pregabalin and alpha lipoic acid in a weight ratio of pregabalin to alpha lipoic acid from 1:3 to 1:8, preferably 1:5.

In another embodiment, the method of treatment comprises administering pregabalin in an amount from 40 mg to 160 mg, and alpha lipoic acid in an amount from 200 to 800 mg. Preferably, pregabalin is administered in an amount from 65 to 150 mg and alpha lipoic acid is administered in an amount from 400 to 600 mg.

In another embodiment, the method of present invention comprises administering pregabalin and alpha lipoic acid by oral route.

Administration of pregabalin and alpha lipoic acid may occur through a pharmaceutical composition comprising both substances.

In another aspect, the present invention refers to a pharmaceutical composition comprising alpha lipoic acid and pregabalin in synergistically effective amounts.

In another embodiment, the pharmaceutical composition of the invention comprises pregabalin and alpha lipoic acid in a weight ratio of pregabalin to alpha lipoic acid from 1:1.25 to 1:25, preferably 1:5.

In one further embodiment, the pharmaceutical composition according to present invention comprises 40 mg to 160 mg of pregabalin and 200 to 800 mg of alpha lipoic acid. In one particular embodiment, the pharmaceutical composition of the invention comprises 75 to 150 mg of pregabalin and 400 to 600 mg of alpha lipoic acid.

In one particular embodiment, the pharmaceutical composition according to present invention comprises alpha lipoic acid and pregabalin as active principles, and further comprises pharmaceutically acceptable excipients.

Active principles of present invention may be in free form or as a pharmaceutically acceptable salt thereof.

Pharmaceutically acceptable excipients which may be used in the pharmaceutical composition according to present invention include diluents, carriers, solubilizers, emulsifiers, binders, preservatives and/or pharmaceutically acceptable adjuvants. The pharmaceutical composition of present invention may be formulated for oral administration. Pharmaceutical compositions of present invention may be formulated for delivering active principles in sustained or controlled form. Said formulations will be apparent for any one skilled in the art of pharmaceutical formulations.

Examples shown below have a sole purpose of illustrating and demonstrating some embodiments of the invention. Exemplary embodiments shall not be considered limiting of the present invention. As any one skilled in the art may acknowledge, amendments and variations to embodiments described below may be carried out without altering the essence of the invention.

EXAMPLES

Example 1. Antineuropathic Effect of a Combination of Pregabalin and Alpha Lipoic Acid Antineuropathic effect of a combination of pregabalin and alpha lipoic acid through the neuropathic pain model induced by L5/L6 spinal nerve ligation in rat was determined.

Animales

Wistar female rats with a body weight of 120-140 g were used for all experiments. Animals were kept under temperature controlled conditions (22° C.) and water and food were given ad-libitum in experimentation rooms. Experiments were carried out according to the guidelines on ethical issues on experimental pain research in animals (Zimmermann M. 1983. Ethical guidelines for investigations of experimental pain in conscious animals. Pain. 16:109-110).

Drugs

Both pregabalin and alpha lipoic acid were suspended in a 0.5% carboxymethylcellulose isotonic saline solution. Individual drugs or in combination were prepared and administered just before starting the experiment.

L5/L6 Spinal Nerve Ligation

Rats were prepared according to the method described by Kim S H, Chung J M. 1992. An experimental model for peripheral neuropathy produced by segmental spinal nerve ligation in the rat. Pain. 50(3):355-63. On surgery day, the animal was anesthesized with a mixture of ketamine (45 mg/Kg, i.p.) and xylazine (12 mg/Kg, i.p.). Later, an incision was made just on the left side of backbone at level of vertebrae L4-S1. Spinal nerves were carefully ligated with 6-0 silk thread and muscle was then sutured with absorbable thread while skin was sutured with 6-0 silk thread. In the group of falsely operated rats (sham), surgical procedure was identical to that described above, except that backbone nerves were not ligated. Upon surgery termination, rats were placed in individual cages. All rats were allowed a 14-day recovery before assaying the tactile allodynia model and animals which showed motor deficiencies were discarded from the study.

Determination of Tactile Allodynia

Tactile allodynia was determined according to the previously described method by Chaplan S R, Bach F W, Pogrel J W, Chung J M, Yaksh T L. 1994. Quantitative assessment of tactile allodynia in the rat paw. J Neurosci Methods. 53(1):55-63. In this model, rats were placed in observation cages over a metal grid bottom and adapted during 30 min. Paw withdrawal mechanical threshold was measured immediately after and a systemic administration of drugs was carried out. Later, paw withdrawal mechanical threshold was measured at 0.5, 1, 2, 3, 4, 5, 6, 7 and 8 hours. An increase of withdrawal threshold in this model is considered as antinociceptive effect (analgesia). Similarly, the model has a cut value of 15 g and the group of falsely operated rats (sham) determines 100% of antineuropathic effect in the model, while neuropathic rats administered with vehicle represent 0% of antineuropathy.

Results

Graphs of 50% withdrawal threshold in grams (g) in function of time (minutes) were prepared from data obtained. Area under curve was determined from these graphs through trapezoidal method and % of maximum possible effect (% MEP) was calculated using the following formula:

$$\% \text{ MEP} = (\text{Drug AUC} - \text{Neuropathic AUC})/(\text{Sham AUC} - \text{Neuropathic AUC}) \times 100$$

Figure 2:
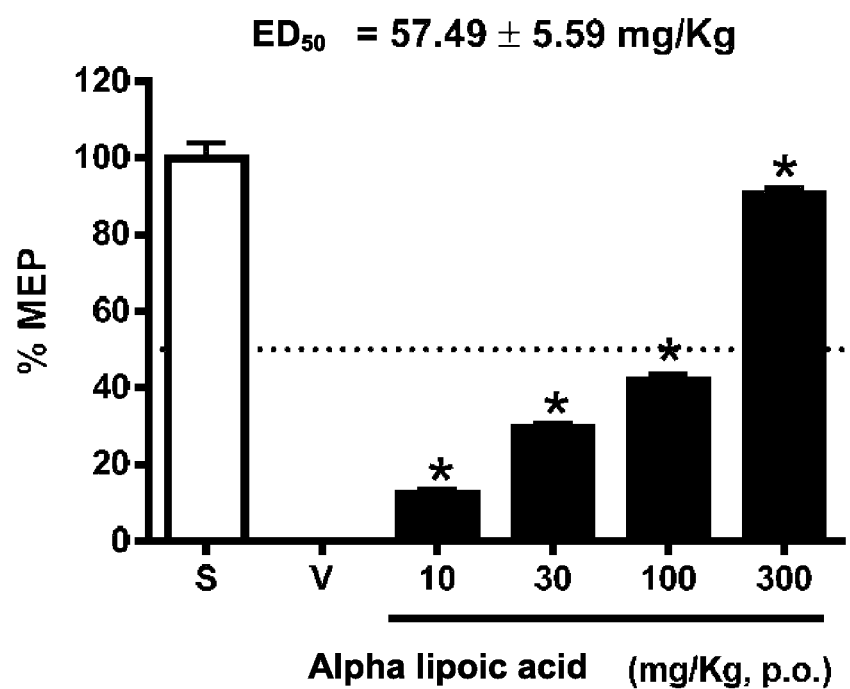
FIG. 2. Dose-response curve showing a percentage of maximum possible anti-neuropathic effect (% MEP) obtained with oral administration of increasing doses of alpha lipoic acid in a neuropathic pain model induced by L5/L6 spinal nerve ligation in rats (ED50=57.49±5.59 mg/kg).
Figure 3:
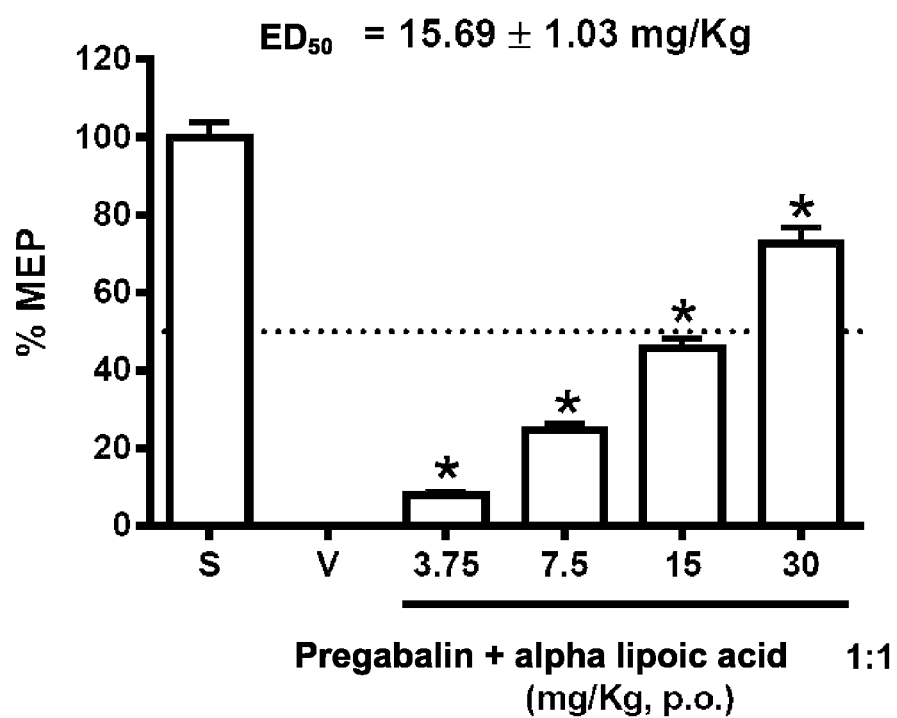
FIG. 3. Dose-response curve showing a percentage of maximum possible anti-neuropathic effect (% MEP) obtained with oral administration of increased doses of a combination pregabalin+alpha lipoic acid (0.15+3.6, 0.3+7.2, 0.6+14.4, and 1.2+28.8 mg/kg, respectively) in a neuropathic pain model induced by L5/L6 spinal nerve ligation. "Y" axis represents the sum of pregabalin+alpha lipoic acid doses in each combination (ED50=15.69±1.03 mg/kg).
Figure 4:
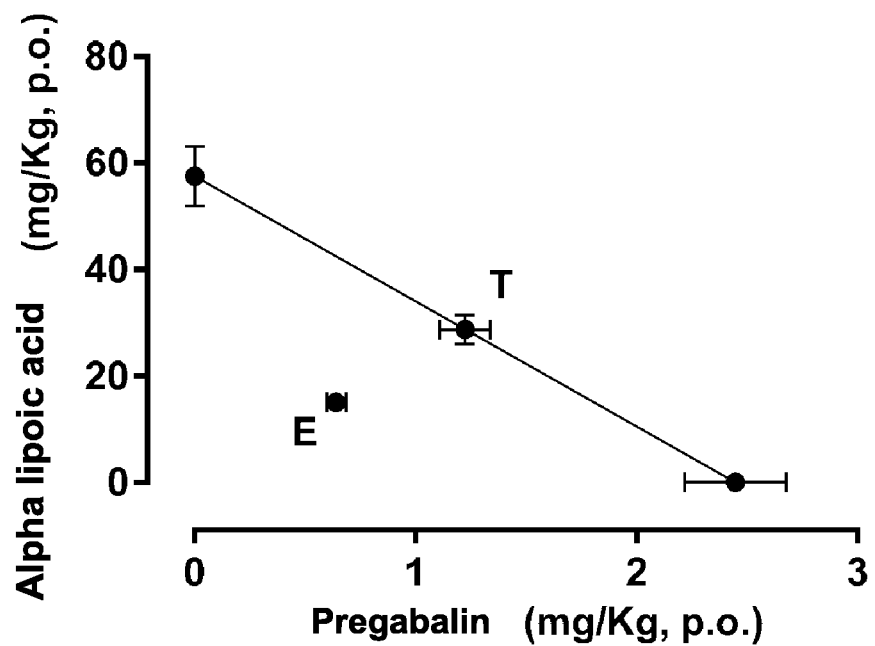
FIG. 4. Isobologram illustrating a synergistic interaction obtained from an orally administered combination of pregabalin+alpha lipoic acid in the neuropathic pain model induced by L5/L6 spinal nerve ligation in rats. Points located over X and Y axes represent experimentally obtained ED50 values for pregabalin and alpha lipoic acid. A diagonal binding ED50 of pregabalin and alpha lipoic acid is the additivity line. Point (T) located halfway in additivity line represents combination theoretical ED50. Point (E) illustrates experimental ED50 for the combination.

Bar graphs and dose-response curves were prepared from % MEP. $ED_{50}$ was calculated from dose-response curves for individual drugs (FIGS. 1 and 2) and theoretical $ED_{50}$ for combination according to the method disclosed by Tallarida RJ. 2000. Drug Synergism and Dose-Effect Data Analysis, ed 1. New York, Chapman & Hall/CRC. pp 1-72. Experimental $ED_{50}$ was calculated from the results obtained from the combination dose-response curve (FIG. 3). Finally, an isobologram was prepared. The isobologram (FIG. 4) graphically demonstrates that the combination produces a synergistic effect. Moreover, interaction index (γ) was equal to 0.524, indicating that the combination enhanced 1.9 times the antineuropathic effect of individual drugs.

Treatments were well-tolerated as to safety, however, alpha lipoic acid induced hair bristling in rats at a 300 mg/Kg dose and one rat was convulsed during the sixth hour at the same dose. As to pregabalin, rats showed sedation and motor discoordination at a dose of 30 mg/Kg. There were no any apparent adverse events in any of the doses tested in the combination.

The invention claimed is:
1. A method of treating neuropathic pain in a human subject in need thereof comprising orally administering to the subject a therapeutic composition consisting of two active ingredients that are:
   a. pregabalin; and
   b. alpha-lipoic acid;
   wherein pregabalin and alpha lipoic acid are administered in a ratio of 1:5 by weight; and wherein pregabalin is administered in an amount from 40 mg to 80 mg and alpha lipoic acid is administered in an amount from 200 mg to 400 mg, and a same dosage of pregabalin and alpha lipoic acid is maintained while treating the neuropathic pain in a human subject in need thereof.

2. The method of claim 1, wherein pregabalin is administered in an amount from 75 mg to 80 mg.

3. A pharmaceutical composition for oral administration for treatment of neuropathic pain wherein the pharmaceutical composition consists of two active ingredients that are:
   a. pregabalin; and
   b. alpha-lipoic acid,
   wherein pregabalin and alpha-lipoic acid are present in a ratio of 1:5; and
wherein pregabalin is in an amount from 40 mg to 80 mg and alpha-lipoic acid is in an amount from 200 mg to 400 mg.

4. The pharmaceutical composition of claim 3, wherein pregabalin is in an amount from 75 mg to 80 mg.

\* \* \* \* \*